(12) United States Patent
Golembiewski

(10) Patent No.: US 7,819,904 B2
(45) Date of Patent: Oct. 26, 2010

(54) LUMBAR SPINE ANTERIOR SCOLIOSIS REDUCTION SURGERY

(76) Inventor: Gary V. Golembiewski, 90 Spring Valley Rd., Park Ridge, NJ (US) 07656

( * ) Notice: Subject to any disclaimer, the term of this patent is extended or adjusted under 35 U.S.C. 154(b) by 215 days.

(21) Appl. No.: 11/947,896

(22) Filed: Nov. 30, 2007

(65) Prior Publication Data

US 2008/0140131 A1 Jun. 12, 2008

Related U.S. Application Data

(60) Provisional application No. 60/921,479, filed on Dec. 1, 2006.

(51) Int. Cl.
*A61B 17/70* (2006.01)
*A61B 17/88* (2006.01)
(52) U.S. Cl. .................. 606/300; 623/17.11; 606/86 A; 606/246; 606/257; 606/279; 606/914
(58) Field of Classification Search ............... 606/86 A, 606/246, 257, 279, 914; 623/17.11
See application file for complete search history.

(56) References Cited

U.S. PATENT DOCUMENTS

| | | | | |
|---|---|---|---|---|
| 5,176,707 | A | * | 1/1993 | Phillips ...................... 606/241 |
| 5,490,851 | A | * | 2/1996 | Nenov et al. ................ 606/252 |
| 5,716,358 | A | * | 2/1998 | Ochoa et al. .................. 606/62 |
| 2006/0269574 | A1 | * | 11/2006 | De Beer et al. .......... 424/239.1 |

* cited by examiner

*Primary Examiner*—Thomas C Barrett
*Assistant Examiner*—Sameh Boles
(74) *Attorney, Agent, or Firm*—Norris McLaughlin & Marcus, PA

(57) ABSTRACT

A method for performing minimally invasive surgery to reduce lumbar scoliosis in a patient is disclosed. The method involves performing an orthopedic exercise or maneuver on a patient to reduce scoliosis, and anchoring the ilioposoas muscles to a region of the femur to permanently reduce the scoliosis. During the exercise or maneuver, a lumbar x-ray is taken on both sides of the patient to determine which side the scoliosis reduction is greatest. The side with the greatest reduction is the side where the surgery takes place.

10 Claims, 5 Drawing Sheets

LUMBAR SPINE ANTERIOR SCOLIOSIS REDUCTION SURGERY

FIELD OF THE INVENTION

The present invention relates to a treatment for scoliosis. More specifically, the present invention relates to a surgical procedure for treating and reducing lumbar scoliosis while avoiding surgery directly on the spinal column.

BACKGROUND OF THE INVENTION

The bones and connective tissue of an adult human spinal column comprises 26 discrete bones, which are anatomically categorized as being members of one of four distinct classifications: cervical, thoracic, lumbar and sacral. The spinal column consists of the bones coupled sequentially to one another by tri-joint complexes that consist of an anterior intervertebral disc and two posterior facet joints. The anterior intervertebral discs of adjacent bones are cushioning cartilage spacers.

The complexity of the spinal column renders it susceptible to several genetic, congenital or developmental irregularities or conditions. One of the most common includes scoliosis, which is a condition that involves complex lateral and rotational curvature and deformity in a human spine. Scoliosis impairs the body's skeletal support and complicates and compromises certain vital functions, such as breathing, circulation and nervous system lesions (subluxations). Additionally, pain is common in adulthood if left untreated. Major causes of scoliosis are idiopathic (i.e., unknown cause), congenital or inherited developmental anomalies, and neuromuscular disorders such as cerebral palsy or spinal muscular atrophy. Due to the health risks and discomfort associated with scoliosis, it is important to treat the afflicted patient in order to reduce or eliminate the condition. With time the scoliosis can become progressively worst.

Spinal surgeries to correct scoliosis are needed by a great many patients. The fact that the spine is a complex construction of bone, cartilage, arteries, veins and nerves surrounded by relatively strong deep intrinsic muscles that support and help move the spine makes spinal surgery difficult to perform and requires a high degree of skill on the part of the surgeon if successful results are to be obtained. Initially, all such spinal surgeries were carried out by what is referred to as "open" procedures wherein the spinal structures being operated upon were exposed via a relatively large skin incision that narrows down in conical fashion to the deep, bony operative target, cutting and destroying intervening soft tissue structures such as muscles, ligaments, arteries, veins and nerves. Formation of the large open incision involves severing and separating a large number of tendons, ligaments, and muscle fibers, and this tissue trauma has been found to cause the patient pain, prolonged hospital stays, prolonged recovery and permanent low back weakness. In addition, elongated spinal rods, sometimes referred to as Harrington rods, are often placed on a patient's spine to correct the scoliosis.

In view of the foregoing, it will be appreciated that there is a need for a method whereby a surgeon may carry out spinal surgery to correct scoliosis with minimal patient trauma. Furthermore, it is desirable that such techniques and apparatus be simple and reliable. Surgeons have been using the anterior lumbar spinal surgery approach for scoliosis since 1969. Advances in medical technology continue to increase the utility of anterior surgical approach in the lumbar spine for a variety of spinal disorders. This is especially true in light of the worldwide acceptance of minimal invasive surgery (MIS).

SUMMARY OF THE INVENTION

The present invention relates to a new and improved method for performing spinal surgery to correct scoliosis in a human patient. Specifically, the method requires minimally invasive techniques to improve or correct the scoliosis. The method comprises the steps of performing a reverse Trendelenberg orthopedic maneuver on a patient; holding the patient's ankle in an elongated position with a traction unit while the patient is performing the reverse Trendelenberg maneuver; taking an anterior to posterior lumbar spine stress end loaded x-ray while the patient's ankle is in traction; determining which side of the lumbar spine reduces scoliosis; performing an incision to reveal the insertion of the ilioposoas muscles; clamping said muscles; and placing an anchoring means at the surgical site to facilitate positioning of the distal end portion of the muscles at or near the lesser trochanter of the patient's femur bone.

Unlike in traditional scoliosis corrective surgeries wherein movement is often restricted to two dimension, the present invention allows for three-dimensional rotational movement in the X, Y, and Z axis. Additionally, post-operative facilitative and compressive nerve lesions are reduced by the present invention. Moreover, because the present invention uses much less hardware than in traditional surgeries, the rate of mechanical failure and infection is reduced.

DETAILED DESCRIPTION OF THE INVENTION

Figure 1:
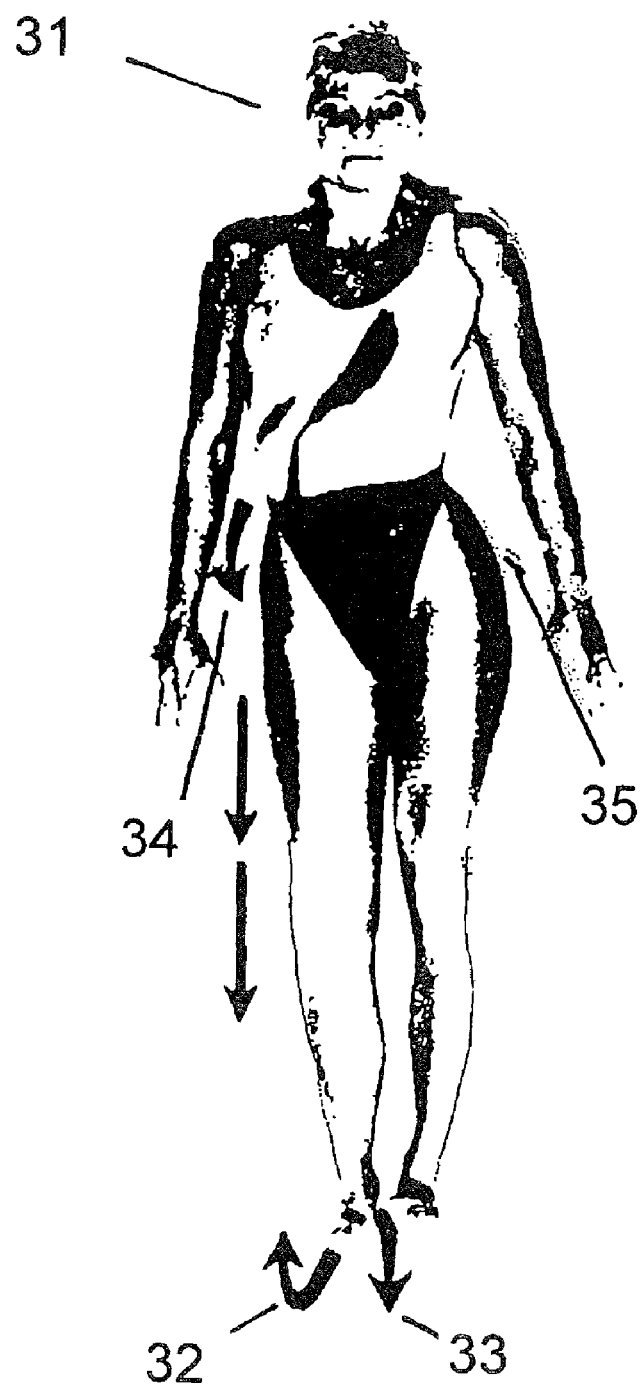
FIG. 1 is a lumbar anterior to posterior standing x-ray showing a right convex scoliosis in a human patient.
Figure 2:
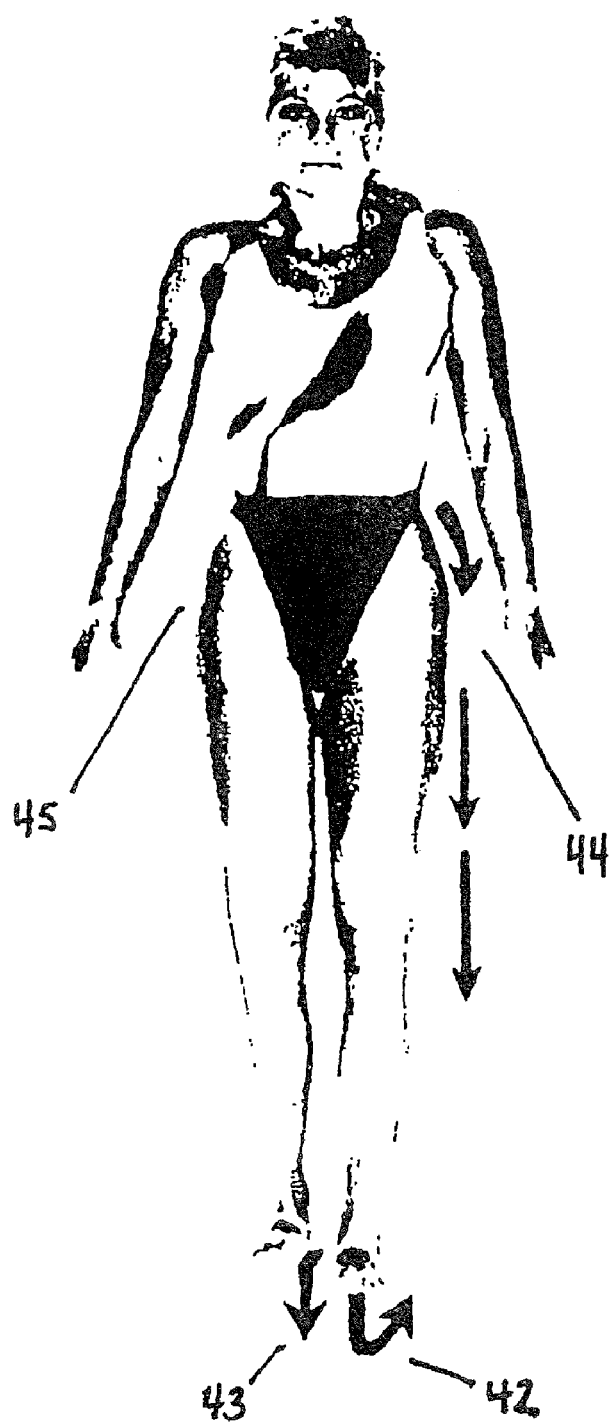
FIG. 2 is a lumbar anterior to posterior stress end loaded left Reverse Trendelenberg orthopedic maneuver x-ray photograph showing a second view of a patient with a right convex scoliosis reduction.
Figure 3:
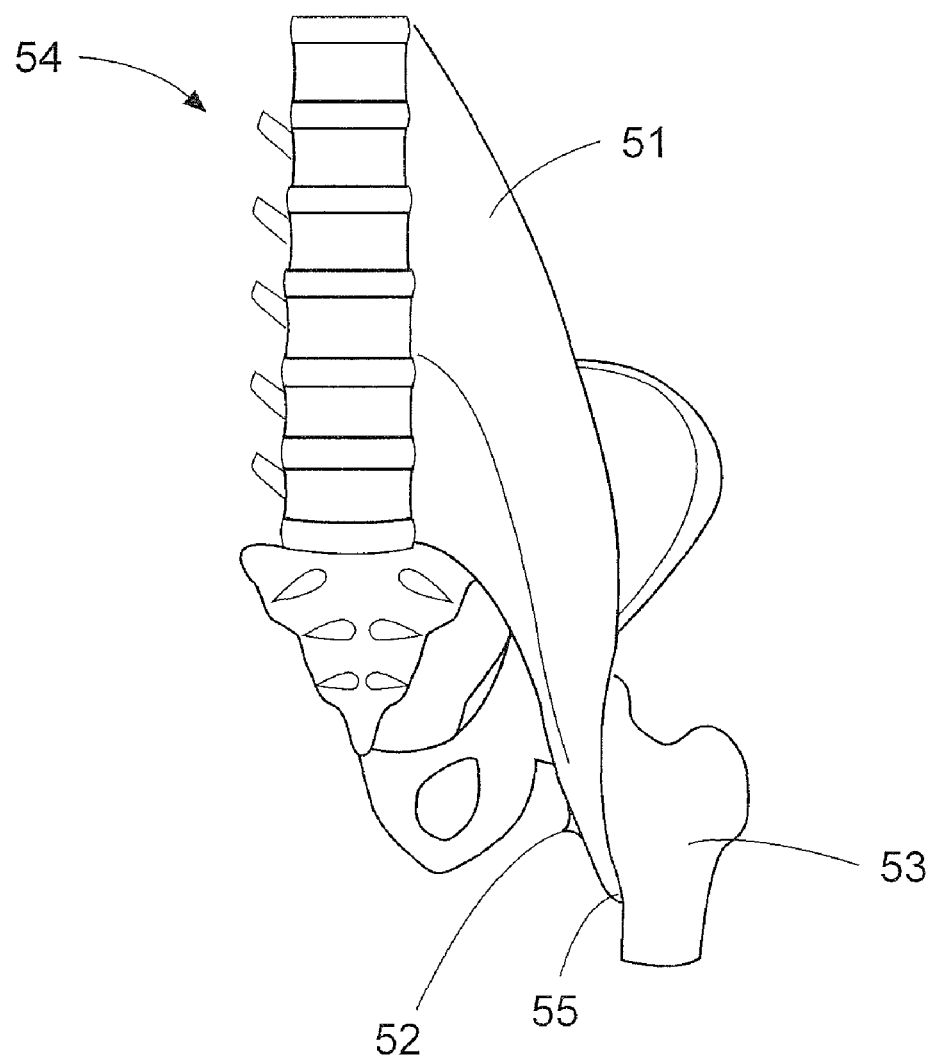
FIG. 3 shows a Reverse Trendelenberg orthopedic maneuver on the right side of a patient.
Figure 4:
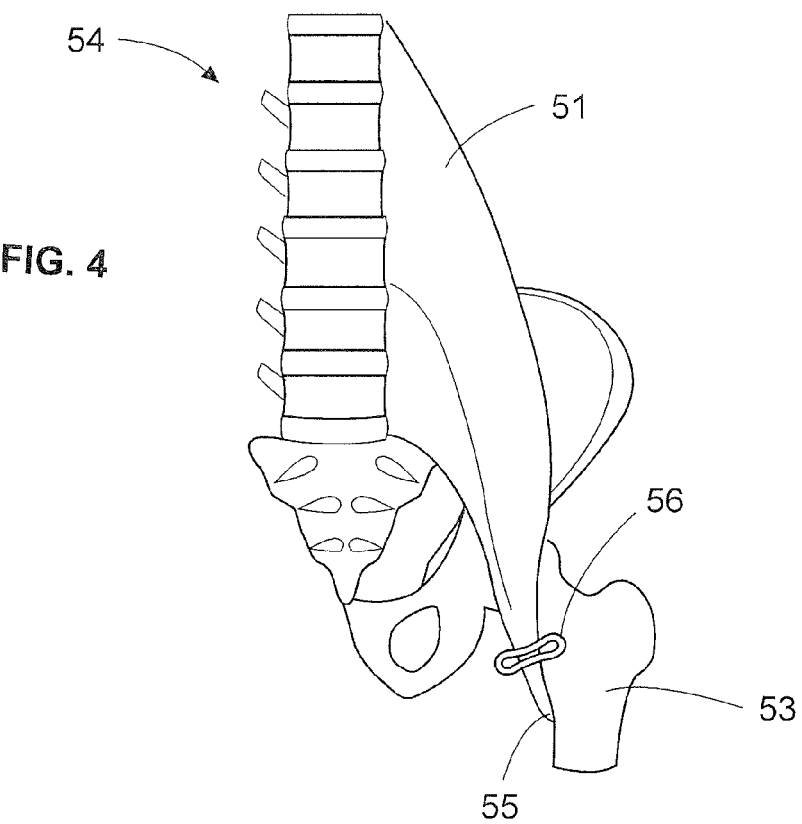
FIG. 4 shows a Reverse Trendelenberg orthopedic maneuver on the left side of a patient.
Figure 5:
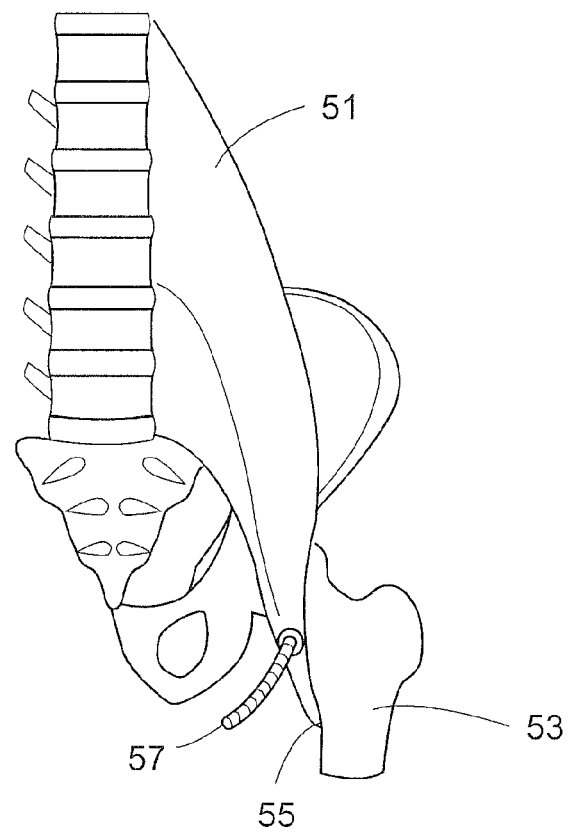
FIG. 5 shows the relevant human anatomical region according to the present invention.
Figure 6:
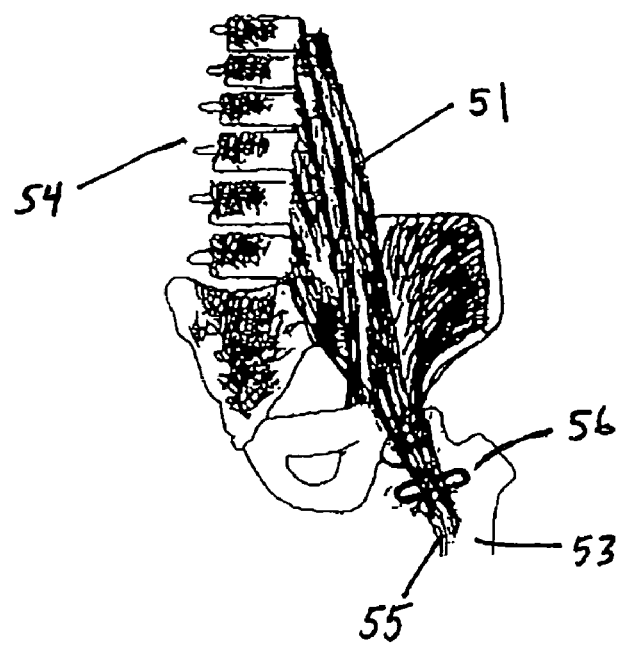
FIG. 6 shows the ilioposoas muscles clamped at or superior to the lesser trochanter.
Figure 7:
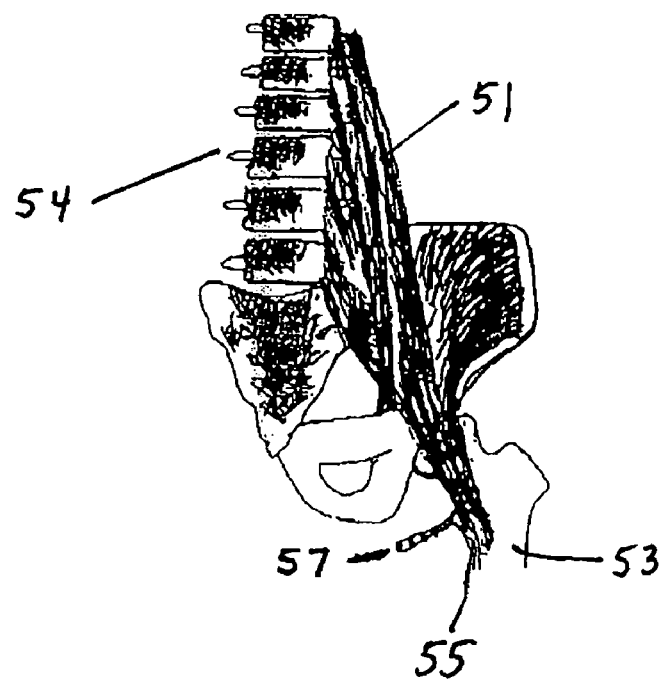
FIG. 7 shows the ilioposoas muscles attached with anchor at or inferior to the lesser trochanter.

A first aspect of the present invention requires that the ilioposoas muscles be brought closer to its insertion point through an elongating, therapeutic exercise called the reverse Trendelenberg maneuver. Referring now to FIG. 3, which shows the reverse Trendelenberg maneuver on a patient's right side, the patient (31) should first lie supine on a firm surface, with both legs straight and arms at sides. The patient is then instructed to position the right foot such that the toes of the right foot are pointed toward the head (32) while concurrently stretching the heel of the right foot downward (33). Next, the patient should move the right hip downward toward the foot (34) while concurrently relaxing the left hip (35). This maneuver is performed on the left side (FIG. 4) in the same manner as described herein, substituting left foot and hip movements for right foot and hip movements (42, 43, 44, 45).

By elongating the hip, leg and heel of a particular side of the patient, the origin of the iliopsoas muscles (51) are brought closer to the insertion, which is on the lesser trochanter (52) of the femur bone (53). The origin of this muscle group, which includes the psoas major, psoas minor and the iliacus, is on the anterior lumbar spine (54). Accordingly, the iliopsoas muscles (51) on the side where the maneuver is performed are shortened.

While the patient is in proper reverse Trendelenberg maneuver position, the patient's ankle is held in a traction unit in the elongated position and a lumbar anterior to posterior x-ray is taken. Any traction unit known to those of ordinary skill in the art can be used in this procedure. The x-ray is taken on both the left and right sides of the patient.

If any reduction of scoliosis is achieved by the reverse Trendelenberg maneuver, the x-ray should show the side where reduction is greatest. This is the side that surgery will be performed on.

Next, the surgical site is prepped according to known procedures. Along with the access surgeon the spine surgeon must define the region of exposure of the anterior superior upper femur/thigh to access the insertion of the iliopsoas muscle group which will be into the lesser trochanter. Together they define the region of exposure and surrounding workspace. It is preferred that the patient be anesthetized either locally or generally prior to the surgery. After the patient is satisfactorily anesthetized, an incision is made on the patient's anterior superior thigh. The incision point can be any point on the anterior superior thigh such that the surgeon has access to the lesser trochanter (52) and is able to expose the insertion of the iliopsoas. The incision should be only large enough to provide the surgeon room to clamp and provide an anchoring means into the lesser trochanter (52) or near the insertion of the iliopsoas. Any known medical or surgical instrument can be used to tighten or shorten the iliopsoas (51). Once the iliopsoas muscles are accessible to the surgeon, the muscles are clamped (56) in the end loaded position with the unilateral traction unit holding the elongated position. By end loaded position is meant the position of the muscles when the patient performs the reverse Trendelenberg maneuver. Because the traction unit is still immobilizing the ankle throughout the surgery, the traction unit stabilizes the end isometric position, thereby reducing the scoliosis. Any surgical clamping means useful for clamping muscles can be used.

After the iliopsoas muscles (51) have been clamped, an anchoring means (57) anchors the muscles at the surgical site to anchor the distal end portion (55) of the muscles near the lesser trochanter (52) of the femur (53). The anchoring means is attached to the clamping means in a manner that allows the clamping means and anchoring means to sufficiently secure the muscles without slippage. The muscles can be anchored either inferior to the lesser trochanter or on the lesser trochanter. Any type of surgical anchoring means suitable for anchoring muscle to bone can be used, and include surgical anchors, surgical screws and surgical staples. After anchoring the muscles, another x-ray of the lumber spine is taken in order to verify the reduction of the scoliosis.

By anchoring the iliopsoas muscles nearer the insertion, the anterior lumber spine is straightened, thus reducing any lumbar scoliosis. Reduction of the lumbar scoliosis, thoracic scoliosis may also be reduced.

While specific embodiments of the present invention have been illustrated and described herein, it is understood that certain changes and modifications may be made therein without departing from the spirit and scope of the invention as show in the following claims.

I claim:

1. A method for performing minimally invasive surgery (MIS) to reduce lumbar scoliosis in a patient, said method comprising the steps of:
    a) performing a reverse Trendelenberg orthopedic maneuver on a patient;
    b) holding the patient's ankle in an elongated position with a traction unit while the patient is performing the reverse Trendelenberg maneuver;
    c) taking an anterior to posterior lumbar spine stress end loaded x-ray while the patient's ankle is in traction;
    d) determining which side of the lumbar spine reduces scoliosis;
    e) performing an incision to reveal the ilioposoas muscles;
    f) clamping said muscles with a clamping means at or inferior to a patients lesser trochanter of a femur bone; and
    g) positioning the distal end portion of the muscles at or inferior to the lesser trochanter by anchoring said muscles with an anchoring means.

2. The method according to claim 1 wherein the anchoring means is a surgical screw.

3. The method according to claim 1 wherein the anchoring means is a surgical anchor.

4. The method according to claim 1 wherein the anchoring means is a surgical staple.

5. The method according to claim 1 wherein the muscles are anchored at or inferior to the lesser trochanter.

6. The method according to claim 1 wherein the muscles are clamped superior or near the lesser trochanter.

7. The method according to claim 1 wherein the muscles are anchored superior to the lesser trochanter.

8. The method according to claim 1 wherein the x-ray is taken on both left and right sides of the patient.

9. The method according to claim 1 wherein after the muscles are anchored a second anterior to posterior lumbar spine stress end loaded x-ray is taken in order to verify reduction of the scoliosis.

10. The method according to claim 1 wherein the anchoring means is attached to the clamping means.

\* \* \* \* \*